United States Patent
Hitzel et al.

(10) Patent No.: US 7,592,000 B2
(45) Date of Patent: Sep. 22, 2009

(54) METHOD OF TANNING HUMAN BODY BY MYSTING OR IMMERSION AT ELEVATED TEMPERATURE

(75) Inventors: Sabine Hitzel, Darmstadt (DE); Hansjürgen Driller, Groβ-Umstadt (DE); Herwig Buchholz, Frankfurt (DE); Silke Hornung, Rödermark (DE); Francois Marchio, Scarsdale, NY (US); Frank Pflücker, Darmstadt (DE); Ralf Rosskopf, Münster (DE)

(73) Assignee: Merck Patent GmbH, Darmstadt (DE)

( * ) Notice: Subject to any disclaimer, the term of this patent is extended or adjusted under 35 U.S.C. 154(b) by 134 days.

(21) Appl. No.: 10/582,500

(22) PCT Filed: Nov. 17, 2004

(86) PCT No.: PCT/EP2004/013006

§ 371 (c)(1),
(2), (4) Date: Jun. 9, 2006

(87) PCT Pub. No.: WO2005/058270

PCT Pub. Date: Jun. 30, 2005

(65) Prior Publication Data

US 2007/0079754 A1   Apr. 12, 2007

(51) Int. Cl.
*A61Q 17/04* (2006.01)
*A61Q 17/00* (2006.01)
*A61Q 19/04* (2006.01)
*A61Q 19/00* (2006.01)
*A61K 8/02* (2006.01)
*A61Q 17/02* (2006.01)
*A61Q 19/02* (2006.01)
*A61Q 19/06* (2006.01)
*A61Q 19/08* (2006.01)
*A61Q 19/10* (2006.01)

(52) U.S. Cl. .......................... 424/59; 424/60; 424/400; 424/401

(58) Field of Classification Search ........... 424/59, 424/60, 400, 401
See application file for complete search history.

(56) References Cited

U.S. PATENT DOCUMENTS

| | | | |
|---|---|---|---|
| 5,229,104 A * | 7/1993 | Sottery et al. ............. | 424/59 |
| 5,232,688 A * | 8/1993 | Ziegler et al. ............. | 424/59 |
| 5,318,774 A | 6/1994 | Alban et al. | |
| 5,741,480 A | 4/1998 | Ascione | |
| 6,403,062 B1 | 6/2002 | Golz-Berner et al. | |
| 6,497,888 B1 | 12/2002 | Morancais et al. | |
| 6,537,528 B2 | 3/2003 | Candau et al. | |
| 2003/0003124 A1 | 1/2003 | Laughlin | |
| 2003/0019504 A1 * | 1/2003 | Laughlin ................. | 132/333 |
| 2004/0028639 A1 | 2/2004 | Maes et al. | |

FOREIGN PATENT DOCUMENTS

| | | |
|---|---|---|
| DE | 690 01 007 T2 | 8/1993 |
| EP | 0 742 002 A | 11/1996 |
| EP | 0 812 586 A1 | 12/1997 |
| EP | 1 092 415 A | 4/2001 |
| EP | 1 277 461 A2 | 1/2003 |
| WO | WO 98/24406 A1 | 6/1998 |
| WO | WO 00/45786 A1 | 8/2000 |

OTHER PUBLICATIONS

Magazine Article; Sundash-"Die Bräunungs-Revolution Aus Den USA!".

* cited by examiner

*Primary Examiner*—Johann R Richter
*Assistant Examiner*—Courtney Brown
(74) *Attorney, Agent, or Firm*—Millen, White, Zelano, Branigan, P.C.

(57) ABSTRACT

The present invention relates to the use of self-tanning substances for application to the human skin, with application taking place at elevated temperature, to corresponding methods of application to the human skin and to a cosmetic formulation which is suitable for said purpose.

22 Claims, No Drawings

METHOD OF TANNING HUMAN BODY BY MYSTING OR IMMERSION AT ELEVATED TEMPERATURE

This application is a National Stage entry of PCT/EP004/13006 filed on 17 Nov. 2004, which claims priority of U.S. Provisional Ser. No. 60/528,472, filed Dec. 11, 2003.

The present invention relates to the use of self-tanning substances for application to the human skin, to corresponding methods of application to the human skin and to a cosmetic formulation which is suitable for said purpose.

The tanning of human skin is regarded as being a sign of wellbeing and health, particularly in regions where pale skin types prevail.

However, natural tanning by the UV radiation present in sunlight also harbours risks, such as premature skin ageing or also of suffering an increased risk of skin cancer.

In order to reduce this risk, UV filter preparations are supplied which are intended to filter harmful parts of UV radiation.

In contrast to this, so-called "pre-tan products" or "tan promoters" are also supplied, which have to be applied prior to solar irradiation. Once in the sun, a yellowing of these preparations occurs, which supposedly leads to a slight brown-yellow coloration of the epidermis, which additionally intensifies the "suntan" and thus shortens the time which the body has to be exposed to the sun.

A further method of artificial tanning, which is entirely independent of UV light, can be brought about by the hormones which are usually released in the body also as a consequence of (natural) UV irradiation and ultimately stimulate the melanocytes to synthesize melanin. Mention would be made in this connection, for example, of modifications of proopiomelanocortin (POMC), such as aMSH and synthetic variants (such as NDP), some of which have much higher activity than natural aMSH. Although these hormones can in principle bring about tanning, their use in cosmetics is precluded since they are all substances with pharmacological activity (hormones), which should not be used widely without medicinal indication.

The colouring of the skin by self-tanning agents also takes place entirely without the action of sunlight. One problem with using self-tanning agents is the even application to the human skin in an adequately high active ingredient concentration.

For example, even application of creams or other preparations by hand is difficult and very time-consuming. In the case of self application, some areas of the body, particularly on the back, cannot be reached at all.

It has also been proposed to apply self-tanning solutions by means of active ingredient showers. However, in this method, large amounts of self-tanning agents are required and even application can likewise only be partially ensured.

Surprisingly, it has now been found that the required active ingredient concentration can be reduced if the self-tanning agents are applied at elevated temperature.

The present invention thus firstly provides for the use of at least one self-tanning substance or a formulation comprising at least one self-tanning substance for application to the human skin, with application taking place at elevated temperature.

The present invention further provides a method of tanning the human body, which is characterized in that at least one self-tanning substance or a formulation comprising at least one self-tanning substance is dissolved in water, the solution is brought to a temperature which is elevated relative to room temperature and the solution is applied to the human body.

The present invention further provides cosmetic formulations which are suitable for the use according to the invention in a particular manner. Cosmetic formulations comprising at least one self-tanning substance, characterized in that the formulation comprises at least one fatty carrier and at least one hydrophilic solvent are therefore claimed.

For the purposes of the present invention, self-tanning substances or self-tanning agents are understood as meaning all substances or mixtures of substances which are able to tan human skin without the effect of UV radiation. Advantageous self-tanning agents which may be used for the purposes of the present invention are the following substances:

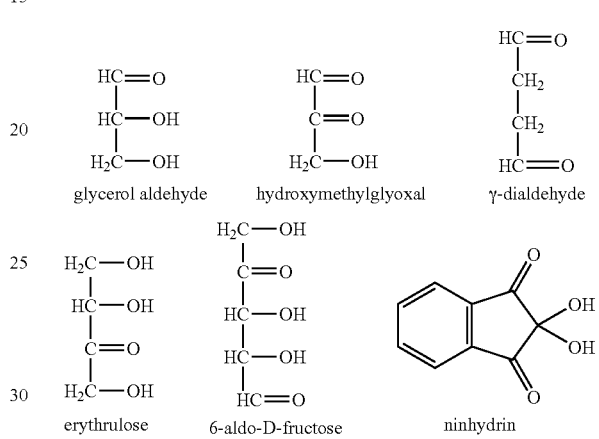

Mention is also made of 5-hydroxy-1,4-naphthoquinone (juglone), which is extracted from the shells of fresh walnuts

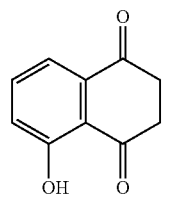

5-hydroxy-1,4-naphthoquinone (juglone)

and the 2-hydroxy-1,4-naphthoquinone (lawsone) which occurs in henna leaves.

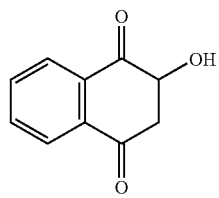

2-hydroxy-1,4-napthoquinone (lawsone)

The most important active ingredient for self-tanning according to the present invention is 1,3-dihydroxyacetone (DHA), a trivalent sugar which occurs in the human body.

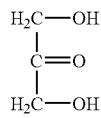

1,3-dihydroxyacetone (DHA)

The concentration of the at least one self-tanning substance preferred according to the invention is in the range from 0.01 to 15% by weight, preferably in the range from 0.05 to 5% by weight and particularly preferably at most 1% by weight. It may be particularly preferred here according to the invention if mixtures of self-tanning substances are used. In particular, it is preferred here to use DHA in a mixture with at least one other self-tanning substance.

It is assumed that the effect, advantageous according to the invention, of the improved tanning effect at elevated temperatures in the case of 1,3-dihydroxyacetone is connected with the following mechanism. As a raw material, DHA is in the form of a powder and consists of dimers. Dissolved in water, some of the dimers convert to the active monomeric form, which brings about the tanning reaction. At an elevated water temperature, the amount of monomers increases. For example, it has been found that in DHA solutions at 30-50° C. up to 30% more active DHA monomers are present than in DHA solutions at 20° C. At the same time, the elevated temperature increases the reaction rate of the tanning reaction.

For this reason, it is preferred according to the invention if the application temperature is in the range between 25 and 60° C. preferably between 30 and 55° C. and particularly preferably between 37 and 50° C.

In addition, it has been found that the equilibrium of the monomer to dimer concentration is established within about 15 minutes following dissolution. It is therefore preferred according to the invention when the solution of the self-tanning substance is tempered for about 15 min, but at least about 10 min, before the solution is applied to the human skin.

In a particularly comfortable manner, said effect can be exploited when used in bath tubs.

The required evenness of tanning can only be achieved with difficulty, or not at all, by mere rubbing. In addition, some areas of the body, in particular on the back, can only be reached with difficulty during self-application of a cream. These problems are avoided with application as bath water. In addition, the application can take place during the customary bathing time, and penetration of the self-tanning agents into the deeper layers of horny skin is favoured by the softening of the skin during bathing.

According to the invention, it is therefore particularly preferred when the solution is applied in a bathtub or whirlpool. The intensive and long-lasting contact of the skin with the active ingredient solution additionally achieves particularly even tanning, which is, in addition, possible with particularly low active ingredient concentrations.

Whirlpools or other baths with an agitated surface in particular offer the additional advantage that no line arises in the neck area, but a continuous fading of the tan arises. If the intention is to also tan the face, then this can be done in a classical way by applying a self-tan-containing cream or by misting with a self-tan solution.

In the corresponding process according to the invention, the human body, as a whole or partially, is immersed into the solution.

Another method, preferred according to the invention, of applying self-tan solutions to the skin is misting, which can take place, for example, by means of a shower or spray gun.

In the corresponding process, for even tanning, the human body—completely or partially—is sprayed evenly with the tempered solution.

The skin tanning achieved in this way cannot be washed off and is removed only with normal shedding of the skin (after about 10-15 days).

The addition of hydrophilic solvents increases the intensity of the tanning. As a result, it is possible to further reduce the concentration of the self-tanning substance. In addition, the hydrophilic solvents are able to ensure a more even distribution of the self-tanning substance, particularly when applied by misting.

The hydrophilic solvents to be used according to the invention can advantageously be chosen from the following groups of substances:
  monoalcohols of low carbon number, e.g. isopropanol,
  polyhydric alcohols, such as, preferably, propylene glycol or glycerol,
  esters of fatty alcohols with alkanoic acids of low carbon number.

The hydrophilic solvents preferred according to the invention are propylene glycol and/or glycerol.

The preferred concentration of hydrophilic solvents, in particular propylene glycol and/or glycerol, in formulations according to the invention is in the range from 0.1 to 50% by weight, more preferred in the range from 0.5 to 20% by weight.

In addition, the presence of so-called fatty carriers should lead to increased tanning intensity. The substances called fatty carriers according to the invention are generally also referred to as "sluices" since they transport the self-tanning agent molecules to deeper layers of the stratum corneum.

Fatty carriers to be mentioned here are, in particular, ceramides, cholesterol, phospholipids, cholesteryl sulphate, cholesteryl phosphate, phosphatidylcholine, lecithin and/or empty liposomes.

According to the invention, phospholipids means the following substances: phosphatidic acids, the actual lecithins, cardolipins, lysophospholipids, lysolecithins, plasmalogens, phosphosphingolipids, sphingomyelins. Preferred substances are described below.

Phosphatidic acids are glycerol derivatives which are esterified in the 1-sn and 2 position with fatty acids (1-sn position: mostly saturated, 2 position: mostly mono- or polyunsaturated), on atom 3-sn by contrast with phosphoric acid and characterized by the general structural formula

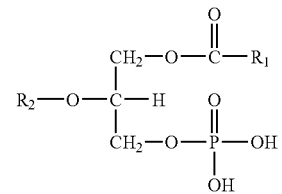

In the phosphatidic acids occurring in human or animal tissue, the phosphate radical is mostly esterified with amino alcohols, such as choline (lecithin=3-sn-phosphatidylcholine) or 2-aminoethanol (ethanolamine) or L-serine (cephalin=3-sn-phosphatidylethanolamine or sn-phosphatidyl-L-serine), with myo-inositol to give the phosphoinositides common in tissues [1-(3-sn-phosphatidyl)-d-myo-inositols], with glycerol to give phosphatidyl-glycerols. Particular preference is given to lecithins (=3-sn-phosphatidyl-choline).

Lecithins are characterized by the general structural formula

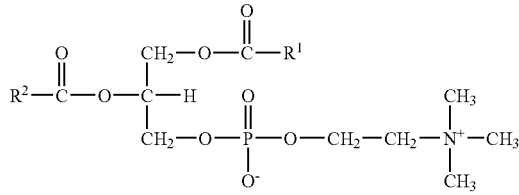

where $R^1$ and $R^2$ are typically unbranched aliphatic radicals having 15 or 17 carbon atoms and up to 4 cis double bonds.

Cardiolipins (1,3-bisphosphatidylglycerols) are phospholipids comprising two phosphatidic acids joined via glycerol.

Lysophospholipids are obtained when an acyl radical is cleaved off from phospholipids by phospholipase A (e.g. lysolecithins). Lysophospholipids are characterized by the general structural formula

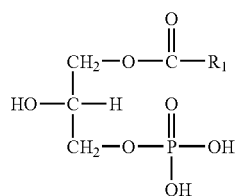

Lysolecithins, for example, are characterized by the general structural formula

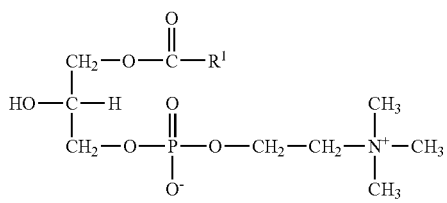

where $R^1$ is typically unbranched aliphatic radicals having 15 or 17 carbon atoms and up to 4 cis double bonds.

The phospholipids also include plasmalogens, in which instead of a fatty acid in the 1 position, an aldehyde (in the form of an enol ether) is bonded; the O-1-sn-alkenyl compounds corresponding to the phosphatidylcholines are, for example, called phosphatidalcholines.

As basic structure, the phosphosphingolipids are based on sphingosine or else phytosphingosine, which are characterized by the following structural formulae:

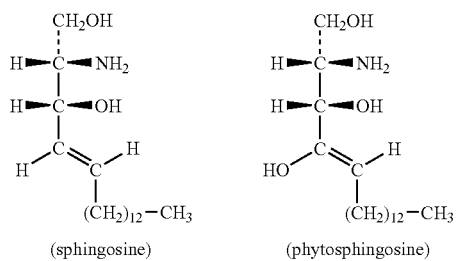

Modifications of sphingolipids are characterized, for example, by the general basic structure

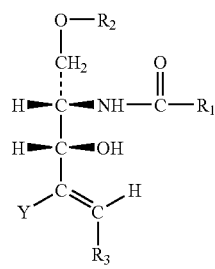

in which $R_1$ and $R_3$, independently of one another, are saturated or unsaturated, branched or unbranched alkyl radicals having 1 to 28 carbon atoms, $R_2$ is chosen from the group: hydrogen atom, saturated or unsaturated, branched or unbranched alkyl radicals having 1 to 28 carbon atoms, sugar radicals, phosphate groups which are unesterified or esterified with organic radicals, sulphate groups which are unesterified or esterified with organic radicals, and Y is either a hydrogen atom, a hydroxyl group or another heterofunctional radical.

Sphingophospholipids

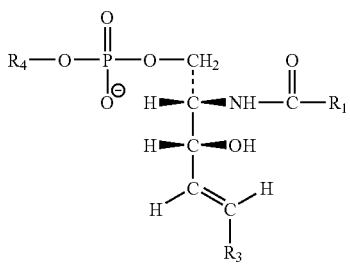

$R_1$ and $R_3$ are alkyl radicals, $R_4$ is an organyl radical.

Sphingomyelins are organylphosphorylated sphingolipids of the type

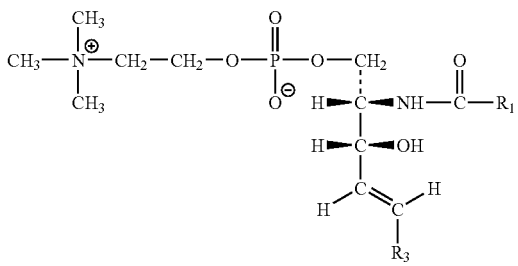

Particularly preferred phospholipids are lecithins. Lecithin types to be used advantageously are chosen from crude lecithins which have been deoiled and/or fractionated and/or spray-dried and/or acetylated and/or hydrolysed and/or hydrogenated. They are commercially available. Preference is given to soya lecithins.

According to the invention, use is advantageously made of ceramides, cholesterol, phospholipids, fatty acids, cholesteryl sulphate, cholesteryl phosphate, phosphatidylcholine, lecithin and/or empty liposomes.

Phospholipids to be used advantageously according to the invention can, for example, be acquired commercially under the trade names Phospholipon 25 or Phospholipon 90 (Natterman), Emulmetik 120 (Lucas Meyer), Stempur E (Stern), Stempur PM (Stem), Nathin 3KE (Stem), Phospholipon 90 H (Nattermann/Rhone-Poulenc), Lipoid S 100 (Lipoid).

According to the invention, the preferred concentration of fatty carriers-is in the range from 0.1 to 50% by weight, more preferred in the range from 0.5 to 10% by weight of fatty carrier.

The preparations according to the invention are suitable on the one hand for the application according to the invention. On the other hand, these formulations, however, are also to be used advantageously in the form of creams since improved absorption and penetration behaviour also facilitate even distribution of a cream.

Under the influence of ultraviolet radiation, DHA can cleave off formaldehyde in small amounts. It is therefore preferred according to the invention when the formulations for the stabilization comprise UV filters. Since these UV filters also come into contact with the skin during application of the formulation, they should be UV filters which are compatible in the topical application. In this connection, an additional advantage which arises is that these UV filters likewise absorb evenly on the skin upon application and thus protect the skin against UV radiation.

Particular preference is given to those UV filters whose physiological safety has already been demonstrated. There are substances known from the specialist literature both for UV-A and also UV-B filters, e.g. benzylidene-camphor derivatives, such as 3-(4'-methylbenzylidene)-dl-camphor (e.g. Eusolex® 6300), 3-benzylidenecamphor (e.g. Mexoryl® SD), polymers of N-{(2 and 4)-[(2-oxoborn-3-ylidene) methyl]benzyl}acrylamide (e.g. Mexoryl® SW), N,N,N-trimethyl-4-(2-oxoborn-3-ylidenemethyl)anilinium methylsulphate (e.g. Mexoryl® SK) or (2-oxoborn-3-ylidene)toluene-4-sulphonic acid (e.g. Mexoryl® SL), benzoyl- or dibenzoylmethanes, such as 1-(4-tert-butylphenyl)-3-(4-methoxyphenyl)propane-1,3-dione (e.g. Eusolex® 9020) or 4-isopropyl-dibenzoylmethane (e.g. Eusolex® 8020), benzophenones, such as 2-hydroxy-4-methoxybenzophenone (e.g. Eusolex® 4360) or 2-hydroxy-4-methoxybenzophenone-5-sulphonic acid and its sodium salt (e.g. Uvinul® MS-40), methoxycinnamic esters, such as octyl methoxycinnamate (e.g. Eusolex® 2292), isopentyl 4-methoxycinnamate, e.g. as a mixture of the isomers (e.g. Neo Heliopan® E 1000), salicylate derivatives, such as 2-ethylhexyl salicylate (e.g. Eusolex® OS), 4-isopropylbenzyl salicylate (e.g. Megasol®) or 3,3,5-trimethylcyclohexyl salicylate (e.g. Eusolex® HMS), 4-aminobenzoic acid and derivatives, such as 4-aminobenzoic acid, 2-ethylhexyl 4-(dimethylamino)benzoate (e.g. Eusolex® 6007), ethoxylated ethyl 4-aminobenzoate (e.g. Uvinul® P25), phenylbenzimidazolesulphonic acids, such as 2-phenylbenzimidazole-5-sulphonic acid and its potassium, sodium and triethanolamine salts (e.g. Eusolex® 232), 2,2-(1,4-phenylene)bisbenzimidazole4,6-disulphonic acid and salts thereof (e.g. Neo Heliopan® AP) or 2,2-(1,4-phenylene) bis-benzimidazole-6-sulphonic acid;

and further substances, such as
2-ethylhexyl 2-cyano-3,3-diphenylacrylate (e.g. Eusolex® OCR),
3,3'-(1,4-phenylenedimethylene)bis(7,7-dimethyl-2-oxo-bicyclo[2.2.1]hept-1-ylmethanesulphonic acid, and its salts (e.g. Mexoryl® SX) and
2,4,6-trianilino(p-carbo-2'-ethylhexyl-1'-oxy)-1,3,5-triazine (e.g. Uvinul® T 150)
hexyl 2-(4-diethylamino-2-hydroxybenzoyl)benzoate (e.g. Uvinul® UVA Plus, BASF).

The compounds listed are only to be regarded as examples. It is of course also possible to use other UV filters.

These organic UV filters are usually incorporated into cosmetic formulations in an amount of from 0.5 to 10% by weight, preferably 1-8%.

Further suitable organic UV filters are, for example,
2-(2H-benzotriazol-2-yl)4-methyl-6-(2-methyl-3-(1,3,3,3-tetramethyl-1-(trimethylsilyloxy)disiloxanyl)propyl) phenol (e.g. Silatrizole®),
bis(2-ethylhexyl) 4,4'-[(6-[4((1,1-dimethylethyl)aminocarbonyl)phenyl-amino]-1,3,5-triazine-2,4-diyl)diimino]bis(benzoate) (e.g. Uvasorb® HEB),
dimethicone diethylbenzalmalonate (CAS No. 207 574-74-1)
2,2'-methylenebis-(6-(2H-benzotriazol-2-yl)-4-(1,1,3,3-tetramethylbutyl)-phenol) (CAS No.103 59745-1 )
2,2'-(1,4-phenylene)bis(1H-benzimidazole4,6-disulphonic acid, mono-sodium salt) (CAS No.180 898-37-7) and
2,4-bis{[4-(2-ethylhexyloxy)2-hydroxy]phenyl}-6-(4-methoxyphenyl)-1,3,5-triazine (CAS No.103 597-45-, 187 393-00-6).

Further suitable UV filters are also methoxyflavones corresponding to the earlier German patent application DE 10232595.2.

Organic UV filters are usually incorporated into cosmetic formulations in an amount of from 0.5 to 20% by weight, preferably 1-15%.

Conceivable inorganic UV filters are those from the group of titanium dioxides, such as, for example, coated titanium dioxide (e.g. Eusolex® T-2000, Eusolex® T-AQUA), zinc oxides (e.g. Sachtotec®), iron oxides and also cerium oxides. These inorganic UV filters are usually incorporated into cosmetic preparations in an amount of from 0.5 to 20% by weight, preferably 2-10%.

Preferred compounds with UV-filtering properties are 3-(4'-methyl-benzylidene)-dl-camphor, 1-(4-tert-butylphenyl)-3-(4-methoxyphenyl) propane-1,3-dione, 4-isopropyldibenzoylmethane, 2-hydroxy-4-methoxy-benzophenone, octyl methoxycinnamate, 3,3,5-trimethylcyclohexyl salicylate, 2-ethylhexyl 4(dimethylamino)benzoate, 2-ethylhexyl 2-cyano-3,3-diphenylacrylate, 2-phenylbenzimidazol-5-sulphonic acid, and its potassium, sodium and triethanolamine salts.

Optimized compositions can, for example, comprise the combination of the organic UV filters 4'-methoxy-6-hydroxy-favone with 1-(4-tert-butylphenyl)-3-(4-methoxyphenyl) propane-1,3dione and 3-(4'-methylbenzylidene)-dl-camphor. This combination gives rise to broadband protection, which can be further enhanced by adding inorganic UV filters, such as titanium dioxide microparticles.

All said UV filters can also be used in encapsulated form. In particular, it is advantageous to use organic UV filters in encapsulated form. Specifically, the following advantages arise:

The hydrophilicity of the capsule wall may be adjusted independently of the solubility of the UV filter. Thus, for example, even hydrophobic UV filters can be incorporated into purely aqueous preparations. In addition, the oily impression, often perceived as being unpleasant, upon application of the preparation comprising hydrophobic UV filters is suppressed.

Certain UV filters, in particular dibenzoylmethane derivatives, exhibit only reduced photostability in cosmetic preparations. By encapsulating these filters or compounds which impair the photostability of these filters, such as, for example, cinnamic acid derivatives, it is possible to increase the photostability of the entire preparation.

The literature discusses time and again the penetration of the skin by organic UV filters and the associated irritancy potential upon direct application to the human skins The encapsulation of the corresponding substances that is proposed here suppresses this effect.

In general, by encapsulating individual UV filters or other ingredients it is possible to avoid preparation problems which arise as a result of individual preparation constituents interacting with one another, such as crystallization operations, precipitations and agglomeration, since the interaction is suppressed.

It is therefore preferred according to the invention when one or more of the abovementioned UV filters are present in encapsulated form. In this connection, it is advantageous if the capsules are so small that they cannot be observed with the naked eye. To achieve the abovementioned effects, it is further necessary that the capsules are sufficiently stable and do not release the encapsulated active ingredient (UV filter), or release it only to a low degree, into the surrounding area.

Suitable capsules can have walls made of inorganic or organic polymers. For example, U.S. Pat. No. 6,242,099 B1 describes the preparation of suitable capsules with walls made of chitin, chitin derivatives or polyhydroxylated polyamines. Capsules which are to be used particularly preferably according to the invention have walls which can be obtained by a sol gel process, as is described in the applications WO 00/09652, WO 00/72806 and WO 00/71084. Preference is given here in turn to capsules whose walls are made of silica gel (silica; undefined silicon oxide hydroxide). The preparation of the corresponding capsules is known to the person skilled in the art, for example from the cited patent applications, the contents of which also expressly belong to the subject-matter of the present application.

In this connection, the capsules are preferably present in preparations according to the invention in amounts which ensure that the encapsulated UV filters are present in the preparation in the amounts given above.

The preparations according to the invention can, moreover, comprise further customary gentle or skincare active ingredients. These may in principle be all active ingredients known to the person skilled in the art.

These may be chromone derivatives. In this connection, the term chromone derivative is preferably understood as meaning certain chromen-2-one derivatives which are suitable as active ingredients for the preventative treatment of human skin and human hair against ageing processes and harmful environmental influences. At the same time, they display a low irritation potential for the skin, have a positive influence on the water binding in the skin, maintain or increase the elasticity of the skin and thus promote skin smoothing. These compounds preferably correspond to the formula I

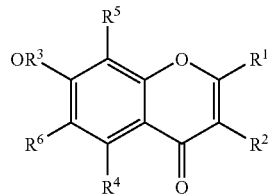

where
$R^1$ and $R^2$ may be identical or different and are chosen from
  H, —C(=O)—$R^7$, —C(=O)—$OR^7$,
  straight-chain or branched $C_1$- to $C_{20}$-alkyl groups,
  straight-chain or branched $C_3$- to $C_{20}$-alkenyl groups,
    straight-chain or branched $C_1$- to $C_{20}$-hydroxyalkyl groups, where the hydroxyl group may be bonded to a primary or secondary carbon atom of the chain and in addition the alkyl chain may also be interrupted by oxygen, and/or
  $C_3$- to $C_{10}$-cycloalkyl groups and/or $C_3$- to $C_{12}$-cycloalkenyl groups, where the rings may in each case also be bridged by —(CH$_2$)$_n$ groups where n=1 to 3,
$R^3$ is H or straight-chain or branched $C_1$- to $C_{20}$-alkyl groups,
$R^4$ is H or $OR^8$,
$R^5$ and $R^6$ may be identical or different and are chosen from
  —H, —OH,
  straight-chain or branched $C_1$- to $C_{20}$-alkyl groups,
  straight-chain or branched $C_3$- to $C_{20}$-alkenyl groups,
  straight-chain or branched $C_1$- to $C_{20}$-hydroxyalkyl groups, where the hydroxyl group may be bonded to a primary or secondary carbon atom of the chain and in addition the alkyl chain may also be interrupted by oxygen and
$R^7$ is H, straight-chain or branched $C_1$- to $C_{20}$-alkyl groups, a polyhydroxy compound, such as preferably an ascorbic acid radical or glycosidic radicals and
$R^8$ is H or straight-chain or branched $C_1$- to $C_{20}$-alkyl groups, where at least 2 of the substituents $R^1$, $R^2$, $R^4$-$R^6$ are different from H, or at least one substituent of $R^1$ and $R^2$ is —C(=O)—$R^7$ or —C(=O)—$OR^7$.

The proportion of one or more compounds chosen from chromone derivatives in the preparation according to the invention is preferably from 0.001 to 5% by weight, particularly preferably from 0.01 to 2% by weight, based on the total preparation.

A protective effect against oxidative stress or against the effect of free radicals of the formulations according to the invention can be achieved when the preparations comprise one or more antioxidants, the person skilled in the art being presented with no difficulties at all in selecting antioxidants which act suitably rapidly or in a time-delayed manner.

There are many proven substances known from the specialist literature which can be used as antioxidants, e.g. amino acids (e.g. glycine, histidine, tyrosine, tryptophan) and derivatives thereof, imidazoles (e.g. urocanic acid) and derivatives thereof, peptides, such as D,L-carnosine, D-camosine, L-carnosine and derivatives thereof (e.g. anserin), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptdes, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), a-hydroxy acids (e.g. citric acid, lactic acid, malic acid), humic acid, bile acid, bile extract, bilirubin, biliverdin, EDTA, EGTA and derivatives thereof, unsaturated fatty acids and derivatives thereof, vitamin C and derivatives (e.g. ascorbyl palmitate, rnagnesium ascorbyl phosphate, ascorbyl acetate), tocopherols and derivatives (e.g. vitamin E acetate), vitamin A and derivatives (e.g. vitamin A pairnitate), and coniferyl benzoate of benzoin resin, rutinic acid and derivatives thereof, α-glycosylrutin, ferulic acid, furfurylideneglucitol, camosine, butylhydroxytoluene, butylhydroxyanisole, nordihydroguaiaretic acid, tri-hydroxybutyrophenone, quercitin, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid (e.g. Oxynex® AP), natural tocopherols, L-(+)-ascorbyl palmitate, L-(+)-ascorbic acid and citric acid (e.g. Oxynex® K LIQUID), tocopherol extracts from natural sources, L-(+)-ascorbyl palmitate, L-(+)ascorbic acid and citric acid (e.g. Oxynex® L LIQUID), DL-α-tocopherol, L-(+)-ascorbyl palmitate, citric acid and lecithin (e.g. Oxynex® LM) or butyihydroxytoluene (BHT), L-(+)-ascorbyl palrnitate and citric acid (e.g. Oxynex® 2004). Antioxidants of this type are used with compounds of the formula I in such compositions usually in ratios in the range from 1000:1 to 1:1000, preferably in amounts of from 100:1 to 1:100.

The preparations according to the invention may comprise vitamins as further ingredients. Preferably, vitamins and vitamin derivatives chosen from vitamin A, vitamin A propionate, vitamin A palmitate, vitamin A acetate, retinol, vitamin B, thiamine chloride hydrochloride (vitamin B$_1$), riboflavin (vitamin B$_2$), nicotinamide, vitamin C (ascorbic acid), vitamin D, ergocalciferol (vitamin D$_2$), vitamin E, DL-α-tocopherol, tocopherol E acetate, tocopherol hydrogensuccinate, vitamin K$_1$, esculin (vitamin P active ingredient), thiamine (vitamin B$_1$), nicotinic acid (niacin), pyridoxine, pyridoxal, pyridoxamine, (vitamin B$_6$), pantothenic acid, biotin, folic acid and cobalamin (vitamin B$_{12}$) are present in the cosmetic preparations according to the invention, particularly preferably vitamin A palmitate, vitamin C and derivatives thereof, DL-α-tocopherol, tocopherol E acetate, nicotinic acid, pantothenic acid and biotin. Vitamins are used here with compounds of the formula I usually in ratios in the range from 1000:1 to 1:1000, preferably in amounts of from 100:1 to 1:100.

Among the phenols with an antioxidative effect, the polyphenols, some of which occur as natural substances, are particularly interesting for applications in the pharmaceutical, cosmetic or nutrition field. For example, the flavonoids or bioflavonoids, known primarily as plant dyes, often have an antioxidative potential. Effects of the substitution pattern of mono- and dihydroxyflavones are dealt with by K. Lemanska, H. Szymusiak, B. Tyrakowska, R. Zielinski, I.M.C.M. Rietjens; Current Topics in Biophysics 2000, 24(2), 101-108. It is observed therein that dihydroxyflavones with an OH group adjacent to the keto function or OH groups in 3'4' or 6,7 or 7,8 position have antioxidative properties, whereas some other mono- and dihydroxyflavones have no antioxidative properties.

Quercetin (cyanidanol, cyanidenolon 1522, meletin, sophoretin, ericin, 3,3',4',5,7-pentahydroxyflavone) is often specified as a particularly effective antioxidant (e.g. C. A. Rice-Evans, N. J. Miller, G. Paganga, Trends in Plant Science 1997, 2(4), 152-159). K. Lemanska, H. Szymusiak, B. Tyrakowska, R. Zielinski, A.E.M.F. Soffers, I.M.C.M. Rietjens; Free Radical Biology & Medicine 2001, 31(7), 869-881 investigate the pH dependency of the antioxidative effect of hydoxyflavones. Over the entire pH range, quercetin exhibits the highest activity of the investigated structures.

Suitable antioxidants are also compounds of the formula II

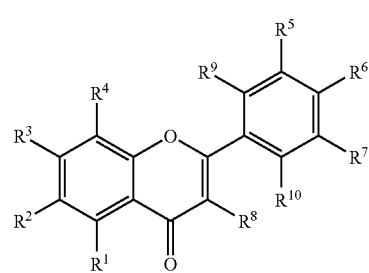

II where $R^1$ to $R^{10}$ may be identical or different and are chosen from
H
OR$^{11}$
straight-chain or branched C$_1$- to C$_{20}$-alkyl groups,
straight-chain or branched C$_3$- to C$_{20}$-alkenyl groups,
straight-chain or branched C$_1$- to C$_{20}$-hydroxyalkyl groups, where the hydroxyl group may be bonded to a primary or secondary carbon atom of the chain and in addition the alkyl chain may also be interrupted by oxygen, and/or
C$_3$- to C$_{10}$-cycloalkyl groups and/or C$_3$- to C$_{12}$-cycloalkenyl groups, where the rings may in each case also be bridged by —(CH$_2$)$_n$ groups where n=1 to 3,
where all OR$^{11}$, independently of one another, are
OH
straight-chain or branched C$_1$- to C$_{20}$-alkyloxy groups, straight-chain or branched $C_3$- to $C_{20}$-alkenyloxy groups, straight-chain or branched $C_1$- to $C_{20}$-hydroxyalkoxy groups, where the hydroxyl group(s) may be bonded to a primary or secondary carbon atom of the chain and in addition the alkyl chain may also be interrupted by oxygen, and/or $C_3$- to $C_{10}$-cycloalkyloxy groups and/or $C_3$- to $C_{12}$-cycloalkenyloxy groups, where the rings may in each case also be bridged by —$(CH_2)_n$ groups where n=1 to 3 and/or mono- and/or oligoglycosyl radicals, with the proviso that at least 4 radicals from $R^1$ to $R^7$ are OH and that at least 2 pairs of adjacent —OH groups are present in the molecule, or $R^2$, $R^5$ and $R^6$ are OH and the radicals $R^1$, $R^3$, $R^4$ and $R^{7-10}$ are H, as are described in the earlier German patent application DE 10244282.7.

Particularly preferred active ingredients are also pyrimidinecarboxylic acids and/or aryl oximes.

Pyrimidinecarboxylic acids occur in halophilic microorganisms and play a role in the osmoregulation of these organisms (E. A. Galinski et al., *Eur. J. Biochem.*, 149 (1985) page 135-139). In this connection, among the pyrimidinecarboxylic acids, mention is made in particular of ectoin ((S)-1,4,5,6-tetrahydro-2-methyl4-pyrimidinecarboxylic acid) and hydroxyectoin ((S,S)-1,4,5,6-tetrahydro-5-hydroxy-2-methyl4-pyrimidinecarboxylic acid and derivatives thereof. These compounds stabilize enzymes and other biomolecules in aqueous solutions and organic solvents. In addition, they stabilize in particular enzymes against denaturing conditions, such as salts, extreme pH values, surfactants, urea, guanidinium chloride and other compounds.

Ectoin and ectoin derivatives, such as hydroxyectoin, can advantageously be used in medicaments. In particular, hydroxyectoin can be used for the preparation of a medicament for the treatment of skin disorders. Other fields of use of hydroxyectoin and other ectoin derivatives are typically in fields in which, for example, trehalose is used as additive. Thus, ectoin derivatives, such as hydroxyectoin, can be used as protectant in dried yeast and bacteria cells. Pharmaceutical products such as non-glycoslated, pharmaceutically active peptides and proteins, e.g. t-PA, can also be protected with ectoin or its derivatives.

Among the cosmetic applications, mention is made in particular of the use of ectoin and ectoin derivatives for the care of aged, dry or irritated skin. For example, European patent application EP-A-0 671 161 describes, in particular, that ectoin and hydroxyectoin are used in cosmetic preparations such as powders, soaps, surfactant containing cleansing products, lipsticks, blusher, foundations, care creams and sunscreen preparations.

In this connection, preference is given to using a pyrimidinecarboxylic acid according to formula III below,

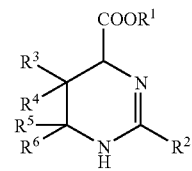

III in which $R^1$ is a radical H or $C_{1-8}$-alkyl, $R^2$ is a radical H or $C_{1-4}$-alkyl and $R^3$, $R^4$, $R^5$ and $R^6$ are in each case independently of one another a radical from the group H, OH, $NH_2$ and $C_{1-4}$-alkyl. Preference is given to using pyrimidinecarboxylic acids in which $R^2$ is a methyl or an ethyl group, and $R^1$ or $R^5$ and $R^6$ are H. Particular preference is given to using the pyrimidine-carboxylic acids ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid). In this connection, the preparations according to the invention comprise pyrimidinecarboxylic acids of this type preferably in amounts up to 15% by weight.

Among the aryl oximes, preference is given to using 2-hydroxy-5-methyllaurophenone oxime, which is also referred to as HMLO, LPO or F5.

Its suitability for use in cosmetic compositions is known, for example, from German laid-open specification DE-A-41 16 123. Preparations which comprise 2-hydroxy-5-methyl-laurophenone oxime are accordingly suitable for the treatment of skin disorders which are accompanied by inflammations. It is known that preparations of this type can be used, for example, for the therapy of psoriasis, various forms of eczema, irritative and toxic dermatitis, UV dermatitis, and other allergic and/or inflammatory disorders of the skin and of skin appendages. In this connection, the preparations preferably comprise 0.01 to 10% by weight of the aryl oxime, it being particularly preferred if the preparation comprises 0.05 to 5% by weight of aryl oxime.

In addition, the preparations according to the invention can also comprise dyes and colour pigments. The dyes and colour pigments can be chosen from the corresponding positive list of the Cosmetics Directive or the EC list of cosmetic colorants. In most cases, they are identical to the dyes permitted for foods. Advantageous colour pigments are, for example, titanium dioxide, mica, iron oxides (e.g. $Fe_2O_3$, $Fe_3O_4$, FeO (OH)) and/or tin oxide. Advantageous dyes are, for example, carmine, Prussian blue, chromium oxide green, ultramarine blue and/or manganese violet. It is particularly advantageous to choose the dyes and/or colour pigments from the following list. The Colour Index numbers (CIN) are taken from the Rowe Colour Index, 3rd edition, Society of Dyers and Colourists, Bradford, England, 1971.

| Chemical or other name | CIN | Colour |
|---|---|---|
| Pigment Green | 10006 | Green |
| Acid Green 1 | 10020 | Green |
| 2,4-Dinitrohydroxynaphthalene-7-sulphonic acid | 10316 | Yellow |
| Pigment Yellow 1 | 11680 | Yellow |
| Pigment Yellow 3 | 11710 | Yellow |
| Pigment Orange 1 | 11725 | Orange |
| 2,4-Dihydroxyazobenene | 11920 | Orange |
| Solvent Red 3 | 12010 | Red |

-continued

| Chemical or other name | CIN | Colour |
|---|---|---|
| 1-(2'-Chloro-4'-nitro-1'-phenylazo)-2-hydroxynaphthalene | 12085 | Red |
| Pigment Red 3 | 12120 | Red |
| Ceres red; Sudan red; Fat Red G | 12150 | Red |
| Pigment Red 112 | 12370 | Red |
| Pigment Red 7 | 12420 | Red |
| Pigment Brown 1 | 12480 | brown |
| 4-(2'-Methoxy-5'-sulphodiethylamido-1'-phenylazo)-3-hydroxy-5''-chloro-2'',4''-dimethoxy-2-naphthanilide | 12490 | red |
| Disperse Yellow 16 | 12700 | yellow |
| 1-(4-Sulpho-1-phenylazo)-4-aminobenzene-5-sulphonic acid | 13015 | yellow |
| 2,4-Dihydroxyazobenzene-4'-sulphonic acid | 14270 | orange |
| 2-(2,4-Dimethylphenylazo-5-sulpho-1-hydroxynaphthalene-4-sulphonic acid | 14700 | Red |
| 2-(4-Sulpho-1-naphthylazo)-1-naphthol-4-sulphonic acid | 14720 | Red |
| 2-(6-Sulpho-2,4-xylylazo)-1-naphthol-5-sulphonic acid | 14815 | Red |
| 1-(4'-Sulphophenylazo)-2-hydroxynaphthalene | 15510 | orange |
| 1-(2-Sulpho-4-chloro-5-carboxy-1-phenylazo)-2-hydroxynaphthalene | 15525 | Red |
| 1-(3-Methylphenylazo-4-sulpho)-2-hydroxynaphthalene | 15580 | Red |
| 1-(4',(8')-Sulphonaphthylazo)-2-hydroxynaphthalene | 15620 | Red |
| 2-Hydroxy-1,2'-azonaphthalene-1'-sulphonic acid | 15630 | Red |
| 3-Hydroxy-4-phenylazo-2-naphthylcarboxylic acid | 15800 | Red |
| 1-(2-Sulpho-4-methyl-1-phenylazo)-2-naphthylcarboxylic acid | 15850 | Red |
| 1-(2-Sulpho-4-methyl-5-chloro-1-phenylazo)-2-hydroxynaphthalene-3-carboxylic acid | 15865 | Red |
| 1-(2-Sulpho-1-naphthylazo)-2-hydroxynaphthalene-3-carboxylic acid | 15880 | Red |
| 1-(3-Sulpho-1-phenylazo)-2-naphthol-6-sulphonic acid | 15980 | orange |
| 1-(4-Sulpho-1-phenylazo)-2-naphthol-6-sulphonic acid | 15985 | yellow |
| Allura Red | 16035 | red |
| 1-(4-Sulpho-1-naphthylazo)-2-naphthol-3,6-disulphonic acid | 16185 | red |
| Acid Orange 10 | 16230 | orange |
| 1-(4-Sulpho-1-naphthylazo)-2-naphthol-6,8-disulphonic acid | 16255 | red |
| 1-(4-Sulpho-1-naphthylazo)-2-naphthol-3,6,8-trisulphonic acid | 16290 | red |
| 8-Amino-2-phenylazo-1-naphthol-3,6-disulphonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulpho-1-phenylazo)-1-(4-sulphophenyl)-5-hydroxy-pyrazolone-3-carboxylic acid | 19140 | yellow |
| Pigment Yellow 16 | 20040 | yellow |
| 2,6-(4'-Sulpho-2'',4''-dimethyl)bisphenylazo)1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulpho-1''-phenylazo)-7'-sulpho-1'-naphthylazo]-1-hydroxy-7-aminonaphthalene-3,6-disulphonic acid | 27755 | black |
| 4-[4''-Sulpho-1''-phenylazo)-7'-sulpho-1'-naphthylazo]-1-hydroxy-8-acetylaminonaphthalene-3,5-disulphonic acid | 28440 | black |
| Direct Orange 34, 39, 44, 46, 60 | 40215 | orange |
| Food Yellow | 40800 | orange |
| trans-β-Apo-8'-carotinaldehyde (C$_{30}$) | 40820 | orange |
| trans-Apo-8'-carotinic acid (C$_{30}$)-ethyl ester | 40850 | orange |
| Canthaxanthin | 40850 | orange |
| Acid Blue 1 | 42045 | blue |
| 2,4-Disulpho-5-hydroxy-4'-4''-bis-(diethylamino)-triphenylcarbinol | 42051 | blue |
| 4-[(-4-N-Ethyl-p-sulphobenzylamino)phenyl-(4-hydroxy-2-sulphophenyl)(methylene)-1-(N-ethyl-N-p-sulphobenzyl)-2,5-cyclohexadienimine] | 42053 | green |
| Acid Blue 7 | 42080 | blue |
| (N-Ethyl-p-sulphobenzylamino)phenyl-(2-sulphophenyl)-methylene-(N-ethyl-N-p-sulphobenzyl)$\Delta^{2,5}$-cyclohexadienimine | 42090 | blue |
| Acid Green 9 | 42100 | green |

-continued

| Chemical or other name | CIN | Colour |
|---|---|---|
| Diethyl-di-sulphobenzyldi-4-amino-2-chlorodi-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulphobenzyl)amino-4"-(N-diethyl)amino-2-methyl-N-ethyl-N-m-sulphobenzyl-fuchsonimmonium | 42735 | blue |
| 4'-(N-Dimethyl)amino-4"-(N-phenyl)aminonaphtho-N-dimethylfuchsonimmonium | 44045 | blue |
| 2-Hydroxy-3,6-disulpho-4,4'-bisdimethylaminonaphtho-fuchsonimmonium | 44090 | green |
| Acid Red 52 | 45100 | red |
| 3-(2'-Methylphenylamino)-6-(2'-methyl-4'-sulphophenyl-amino)-9-(2"-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulphonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminium complex | 58000 | red |
| 3-Oxypyrene-5,8,10-sulphonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulpho-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulphonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanine | 74260 | green |
| Natural Yellow 6, 19; Natural Red 1 | 75100 | yellow |
| Bixin, Norbixin | 75120 | orange |
| Lycopene | 75125 | yellow |
| trans-alpha-, beta- and gamma-carotene | 75130 | orange |
| Keto- and/or hydroxyl derivatives of carotene | 75135 | yellow |
| Guanine or pearlescent agent | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a und b; copper compounds of chlorophylls and chlorophyllins | 75810 | green |
| Aluminium | 77000 | white |
| Hydrated alumina | 77002 | white |
| Hydrous aluminium silicate | 77004 | white |
| Ultramarine | 77007 | blue |
| Pigment Red 101 and 102 | 77015 | red |
| Barium sulphate | 77120 | white |
| Bismuth oxychloride and its mixtures with mica | 77163 | white |
| Calcium carbonate | 77220 | white |
| Calcium sulphate | 77231 | white |
| Carbon | 77266 | black |
| Pigment Black 9 | 77267 | black |
| Carbo medicinalis vegetabilis | 77268 | black |
| Chromium oxide | 77288 | green |
| Chromium oxide, hydrous | 77278 | green |
| Pigment Blue 28, Pigment Green 14 | 77346 | green |
| Pigment Metal 2 | 77400 | brown |

-continued

| Chemical or other name | CIN | Colour |
|---|---|---|
| Gold | 77480 | brown |
| Iron oxides and hydroxides | 77489 | orange |
| Iron oxide | 77491 | red |
| Iron oxide hydrate | 77492 | yellow |
| Iron oxide | 77499 | black |
| Mixtures of iron(II)- and iron(III)hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavine | | yellow |
| Sugar colouring | | brown |
| Capsanthin, capsorubin | | orange |
| Betanin | | red |
| Benzopyrylium salts, anthocyans | | red |
| Aluminium, zinc, magnesium and calcium stearate | | white |
| Bromothymol blue | | blue |

It may also be favourable to choose as dye one or more substances from the following group: 2,4-dihydroxyazobenzene, 1-(2'-chloro-4'-nitro-1'-phenylazo)-2-hydroxynaphthalene, Ceres Red, 2-(4-sulpho-1-naphthylazo)-1-naphthol-4-sulphonic acid, calcium salt of 2-hydroxy-1,2'-azonaphthalene-1'-sulphonic acid, calcium and barium salts of 1-(2-sulpho4-methyl-1-phenylazo)-2-naphthylcarboxylic acid, calcium salt of 1-(2-sulpho-1-naphthylazo)-2-hydroxynaphthalene-3-carboxylic acid, aluminium salt of 1-(4-sulpho-1-phenylazo)-2-naphthol-6-sulphonic acid, aluminium salt of 1-(4-sulpho-1-naphthylazo)-2-naphthol-3,6-disulphonic acid, 1-(4-sulpho-1-naphthylazo)2-naphthol-6,8-disulphonic acid, aluminium salt of 4-(4-sulpho-1-phenylazo)-1-(4-sulphophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, aluminium salt of 2,4,5,7-tetraiodofluorescein, aluminium salt of quinophthalone disulphonic acid, aluminium salt of indigo disulphonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extract, β-carotene or cochineal.

Also advantageous for the purposes of the present invention are gel creams with a content of pearlescent pigments. Preference is given in particular to the types of pearlescent pigments listed below:

1. Natural pearlescent pigments, such as, for example
   1. "pearl essence" (guanine/hypoxanthin mixed crystals from fish scales) and
   2. "mother of pearl" (ground mussel shells)
2. Monocrystalline pearlescent pigments, such as, for example, bismuth oxychloride (BiOCl)
3. Layer-substrate pigments: e.g. mica/metal oxide.

Bases for pearlescent pigments are, for example, pulverulent pigments or castor oil dispersions of bismuth oxychloride and/or titanium dioxide, and bismuth oxychlodide and/or titanium dioxide on mica. The lustre pigment listed under CIN 77163, for example, is particularly advantageous.

Also advantageous are, for example, the following types of pearlescent pigment based on mica/metal oxide:

| Group | Coating/layer thickness | Colour |
|---|---|---|
| Silver-white pearlescent pigments | $TiO_2$: 40-60 nm | silver |
| Interference pigments | $TiO_2$: 60-80 nm | yellow |
| | $TiO_2$: 80-100 nm | red |
| | $TiO_2$: 100-140 nm | blue |
| | $TiO_2$: 120-160 nm | green |
| Colour lustre pigments | $Fe_2O_3$ | bronze |
| | $Fe_2O_3$ | copper |
| | $Fe_2O_3$ | red |
| | $Fe_2O_3$ | red-violet |
| | $Fe_2O_3$ | red-green |
| | $Fe_2O_3$ | black |
| Combination pigments | $TiO_2/Fe_2O_3$ | gold shades |
| | $TiO_2/Cr_2O_3$ | green |
| | $TiO_2$/Prussian blue | deep blue |

Particular preference is given, for example, to the pearlescent pigments obtainable from Merck under the trade names Timiron, Colorona or Dichrona.

The list of given pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like. $SiO_2$ particles coated with, for example, $TiO_2$ and $Fe_2O_3$ ("ronaspheres"), which are marketed by Merck and are particularly suitable for the optical reduction of fine lines, are advantageous.

It can moreover be advantageous to dispense completely with a substrate such as mica. Particular preference is given to pearlescent pigments which are prepared using $SiO_2$. Such pigments, which may also additionally have goniochromatic effects, are available, for example, under the trade name Sicopearl Fantastico from BASF.

In addition, pigments from Engelhard/Mearl based on calcium sodium borosilicate which have been coated with titanium dioxide can advantageously be used. These are available under the name Reflecks. In addition to the colour, they have a glitter effect as a result of their particle size of 40-80 μm.

In addition, also particularly advantageous are effect pigments which are obtainable under the trade name Metasomes Standard/Glitter in various colours (yellow, red, green, blue) from Flora Tech. The glitter particles are present here in mixtures with various auxiliaries and dyes (such as, for example, the dyes with the Colour Index (CI) Numbers 19140, 77007, 77289, 77491).

The dyes and pigments may be present either individually or in a mixture, and can be mutually coated with one another, different coating thicknesses generally giving rise to different colour effects. The total amount of dyes and colour-imparting pigments is advantageously chosen from the range from e.g. 0.1% by weight to 30% by weight, preferably from 0.5 to 15% by weight, in particular from 1.0 to 10% by weight, in each case based on the total weight of the preparations.

All compounds or components which can be used in the preparations are either known and available commercially or can be synthesized by known processes.

The preparations according to the invention can, moreover, comprise further customary skin-friendly or skincare active ingredients. These may in principle be all active ingredients known to the person skilled in the art.

The cosmetic formulation of the present invention may be in the form of liquid, creamy, milky or gel-like bath additives which are added as liquid together with the bath water, or-in bath capsules which preferably consist of gelatin and which dissolve in the bathwater and release the cosmetic formulation of the present invention.

The present invention thus further provides a cosmetic formulation comprising at least one self-tanning substance, characterized in that the formulation is liquid, creamy, milky and/or gel-like bath additives, bath tablets, bath salts and/or bath capsules.

One possible composition of the liquid formulation comprises up to 75% surfactants (anionic, cationic, nonionic or amphoteric), up to 10% viscosity agents, such as fatty alcohols, up to 5% combability and conditioning agents, up to 5% further ingredients, such as refatting agents, thickeners, opacifiers or pigments, up to 5% perfume oils, up to 1% preservatives, up to 0.5% sequestrants, up to 1% dyes, 0.1-1% DHA, UV filters, 0.1-20% propylene-glycol and/or glycerol and 0.1 and 10% fatty carriers and is made up to 100% with water.

The cosmetic formulation of the present invention may also be present in bath additives such as bath tablets or bath salts. One possible composition of the solid formulation comprises up to 90% sodium salts (e.g. sodium carbonate, bicarbonate, sesquicarbonate, chloride, thiosulphate, borate, phosphate or citrate), up to 40% organic acids (e.g. tartaric acid, citric acid) for effervescent preparations, up to 5% perfume oils (essential oils), up to 5% skincare substances, up to 5% plant oils, up to 5% fillers and for tablets, disintegration auxiliaries (e.g. dextrin, silica, cellulose, gum), up to 5% binders, up to 2% surfactants, up to 1% dyes, 0.1-1% DHA, UV filters, 0.1-20% propylene glycol and/or glycerol and 0.1 and 10% fatty carriers.

In addition, it is preferred when the self-tanning formulations comprise moisture-donating substances, such as, for example, erythrulose or the abovementioned ectoins.

Particularly in the case of application as a bath, it may be further preferred for a water-repelling preparation to be applied to parts of the body which are not to be tanned, or are to be tanned only slightly. Such preparations can be prepared on the basis of silicones, paraffins, various organic polymers, petroleum or fatty acid salts, such as stearates. During bathing, they prevent or reduce the treated skin coming into contact with the self-tanning agent and thus the achieved tanning. Particularly on parts of the body with thickened horny skin, such a pretreatment may be advisable in order to prevent intense coloration of these areas.

As well as the self-tanning preparation, for bath use in particular, it may also be advantageous to also add amino acids, oligoamino acids or proteins, which react in situ with the self-tanning agent. Compounds to be added in preference here are in particular lysine, glycine, methionine and methionine sulphoxide. An advantageous dosing form here is a two-layer tablet, one layer of which comprises the self-tanning agent, and the other layer of which comprises the amino acids.

The examples below serve to illustrate the present invention in more detail without limiting its scope.

EXAMPLE

Foam bath

| Ingredient | [%] |
| --- | --- |
| Dihydroxyacetone | 0.1-1 |
| Surfactant | 10-20 |
| Phospholipids | 5 |
| Preservative | q.s. |
| Colorant | q.s. |
| Perfume oil | q.s. |
| Water | ad 100 |

Preparation:
The ingredients are mixed.

Formulation for misting in active-ingredient showers

| Ingredient | [%] |
| --- | --- |
| Dihydroxyacetone | 5 |
| Propylene glycol | 10 |
| Phospholipids | 5 |
| Preservative | q.s. |
| Perfume oil | q.s. |
| Water | ad 100 |

Preparation:
The ingredients are mixed.

The invention claimed is:

1. A method of tanning the human body, wherein at least one self-tanning substance or a formulation comprising at least one self-tanning substance is dissolved in water, the solution is brought to a temperature which is 30-55° C. and the solution is applied to the human body.

2. A method according to claim 1, wherein application takes place in a bathtub or whirlpool.

3. A method according to claim 1, wherein application to the skin takes place by misting.

4. A method according to claim 1, wherein the human body, as a whole or partially, is immersed into the solution.

5. A method according to claim 1, wherein for even tanning, the human body—completely or partially—is sprayed evenly with the tempered solution.

6. A method according to claim 1, wherein a water-repellent preparation is applied to parts of the body which are not to be tanned or tanned only slightly.

7. A method according to claim 1, wherein the formulation comprises, as hydrophilic solvent, glycerol and/or propylene glycol.

8. A method according to claim 1, wherein the formulation comprises 0.1 to 50% by weight of fatty carrier.

9. A method according to claim 1, wherein the self-tanning substance is 1,3-dihydroxyacetone.

10. A method according to claim 1, wherein the concentration of the self-tanning substance is from 0.01 to 10% by weight.

11. A method according to claim 1, wherein the application temperature is between 37 and 50° C.

12. A method according to claim 10, wherein the concentration of the self-tanning substance is from 0.05 to 5% by weight.

13. A method according to claim 8, wherein the formulation comprises from 0.5 to 10% by weight of fatty carrier.

14. A method according to claim 7, comprising from 0.1 to 50% by weight of said hydrophilic solvent.

15. A method according to claim 14, comprising from 0.5 to 20% by weight of said hydrophilic solvent.

16. A method according to claim 1, wherein said self tanning substance is glycerol aldehyde, hydroxymethylglyoxal, γ-dialdehyde, erythrulose, 6-aldo-D-fructose, ninhydrin, 5-hydroxy-1,4-naphthoquinone (juglone), or 2-hydroxy-1,4-naphthoquinone (lawsone).

17. A method according to claim 1, wherein said formulation is creamy, milky, gel-like, a bath tablet, a bath salt and/or a bath capsule.

18. A method according to claim 17, wherein said formulation is a bath tablet, bath salt, or bath capsule.

19. A cosmetic formulation comprising at least one self-tanning substance wherein the formulation is creamy, milky and/or gel-like, a bath tablet, a bath salt and/or a bath capsule.

20. A cosmetic formulation according to claim 19, comprising at least one self-tanning substance, at least one fatty carrier and at least one hydrophilic solvent.

21. A cosmetic formulation according to claim 20, wherein the fatty carrier present is one or more compounds chosen from the ceramides, cholesterol, phospholipids, cholesteryl sulphate, cholesteryl phosphate, phosphatidylcholine, lecithin and/or empty liposomes.

22. A cosmetic formulation according to claim 19, wherein the formulation is a bath tablet, a bath salt and/or a bath capsule.

* * * * *